(12) United States Patent
Kraus et al.

(10) Patent No.: US 7,192,413 B2
(45) Date of Patent: Mar. 20, 2007

(54) NEEDLE GUARD HAVING INHERENT PROBE DIRECTING FEATURES

(75) Inventors: Robert G. Kraus, Attleboro, MA (US); Alan J. Dextradeur, Franklin, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 327 days.

(21) Appl. No.: 10/459,406

(22) Filed: Jun. 11, 2003

(65) Prior Publication Data
US 2004/0254522 A1 Dec. 16, 2004

(51) Int. Cl.
*A61M 5/00* (2006.01)
*A31M 31/00* (2006.01)
*A61M 37/00* (2006.01)

(52) U.S. Cl. .................. 604/9; 604/93.01; 604/116

(58) Field of Classification Search .............. 604/8–10, 604/93.01, 116, 117, 131, 513, 502, 506, 604/508, 288.01–288.04; 606/159, 167, 606/170, 184, 185
See application file for complete search history.

(56) References Cited

U.S. PATENT DOCUMENTS

| 3,886,948 A | 6/1975 | Hakim |
| 4,332,255 A | 6/1982 | Hakim et al. |
| 4,364,395 A | 12/1982 | Redmond et al. |
| 4,387,715 A | 6/1983 | Hakim et al. |
| 4,464,168 A | 8/1984 | Redmond et al. |
| 4,551,128 A | 11/1985 | Hakim et al. |
| 4,595,390 A | 6/1986 | Hakim et al. |
| 4,615,691 A | 10/1986 | Hakim et al. |

(Continued)

FOREIGN PATENT DOCUMENTS

WO  WO 93/21973 A1  11/1993

(Continued)

OTHER PUBLICATIONS

Gil, Ziv et al., "Ventricular catheter placement in children with hydrocephalus and small ventricles: the use of a frameless neuronavigation system," Child's Nerv Syst 18:26-29 (2002).

(Continued)

*Primary Examiner*—Tatyana Zalukaeva
*Assistant Examiner*—Leslie R. Deak
(74) *Attorney, Agent, or Firm*—Nutter, McClennen & Fish LLP

(57) ABSTRACT

A needle or puncture guard that has inherent probe directing features for use in an in-line configured shunt valve is provided. The guard comprises a base member configured for mounting within the domed reservoir of the shunt valve, and a guide wall seated on the base member. The guide wall is defined by a top wall, an inner side wall, and an opposed outer side wall. The inner side wall has an indented section with an aperture extending through the indented section. The inner side wall can be concavely curved, while the indented section has a curvature that directs instruments that are pressed against the guide wall towards the aperture. A method for performing catheter revisions on a shunt system having a guard within the shunt valve is provided as well. Also provided is a method for placement of an intracranial pressure sensor percutaneously into a ventricular catheter for determining intracranial pressure.

25 Claims, 6 Drawing Sheets

U.S. PATENT DOCUMENTS

| | | | |
|---|---|---|---|
| 4,636,194 A | | 1/1987 | Schulte et al. |
| 4,698,058 A | | 10/1987 | Greenfeld et al. |
| 4,741,730 A | | 5/1988 | Dormandy |
| 4,772,257 A | | 9/1988 | Hakim et al. |
| 4,816,016 A | | 3/1989 | Schulte et al. |
| 4,832,054 A | | 5/1989 | Bark |
| 4,867,740 A | | 9/1989 | East |
| 5,069,603 A | | 12/1991 | Schuetz et al. |
| 5,069,663 A | | 12/1991 | Sussman |
| 5,176,627 A | * | 1/1993 | Watson .................... 604/8 |
| 5,281,205 A | * | 1/1994 | McPherson ............. 604/267 |
| 5,304,114 A | | 4/1994 | Cosman |
| 5,385,541 A | | 1/1995 | Kirsch et al. |
| 5,607,393 A | * | 3/1997 | Ensminger et al. .... 604/288.04 |
| 5,795,307 A | | 8/1998 | Krueger |
| 5,848,989 A | * | 12/1998 | Villani ................. 604/288.02 |
| 5,928,182 A | | 7/1999 | Kraus et al. |
| 6,053,901 A | | 4/2000 | Finch, Jr. et al. |
| 6,056,718 A | * | 5/2000 | Funderburk et al. ..... 604/93.01 |
| 6,190,353 B1 | | 2/2001 | Makower et al. |
| 6,206,885 B1 | | 3/2001 | Ghahremani et al. |
| 6,585,677 B2 | | 7/2003 | Cowan, Jr. et al. |
| 6,588,432 B1 | * | 7/2003 | Rehder et al. ............. 128/899 |
| 6,690,185 B1 | * | 2/2004 | Khandros et al. .......... 324/758 |

FOREIGN PATENT DOCUMENTS

| | | |
|---|---|---|
| WO | WO-01/78684 | 10/2001 |

OTHER PUBLICATIONS

Hudgins, Roger J. et al., "Shunt Revision by Coagulation with Retention of the Ventricular Catheter," Pediatric Neurosurg 19:57-59 (1998).

Martinez-Lage, Juan F. et al., "Prevention of intraventricular hemorrhage during CSF shunt revisions by means of a flexible coagulating electrode," Child's Nerv Syst 14:203-206 (1998).

Ventureyra, Enrique C.G., M.D., et al. , "A New Ventricular Catheter for the Prevention and Treatment of Proximal Obstruction in Cerebrospinal Fluid Shunts," Neurosurgery, 34(5):924-926 (1994).

* cited by examiner

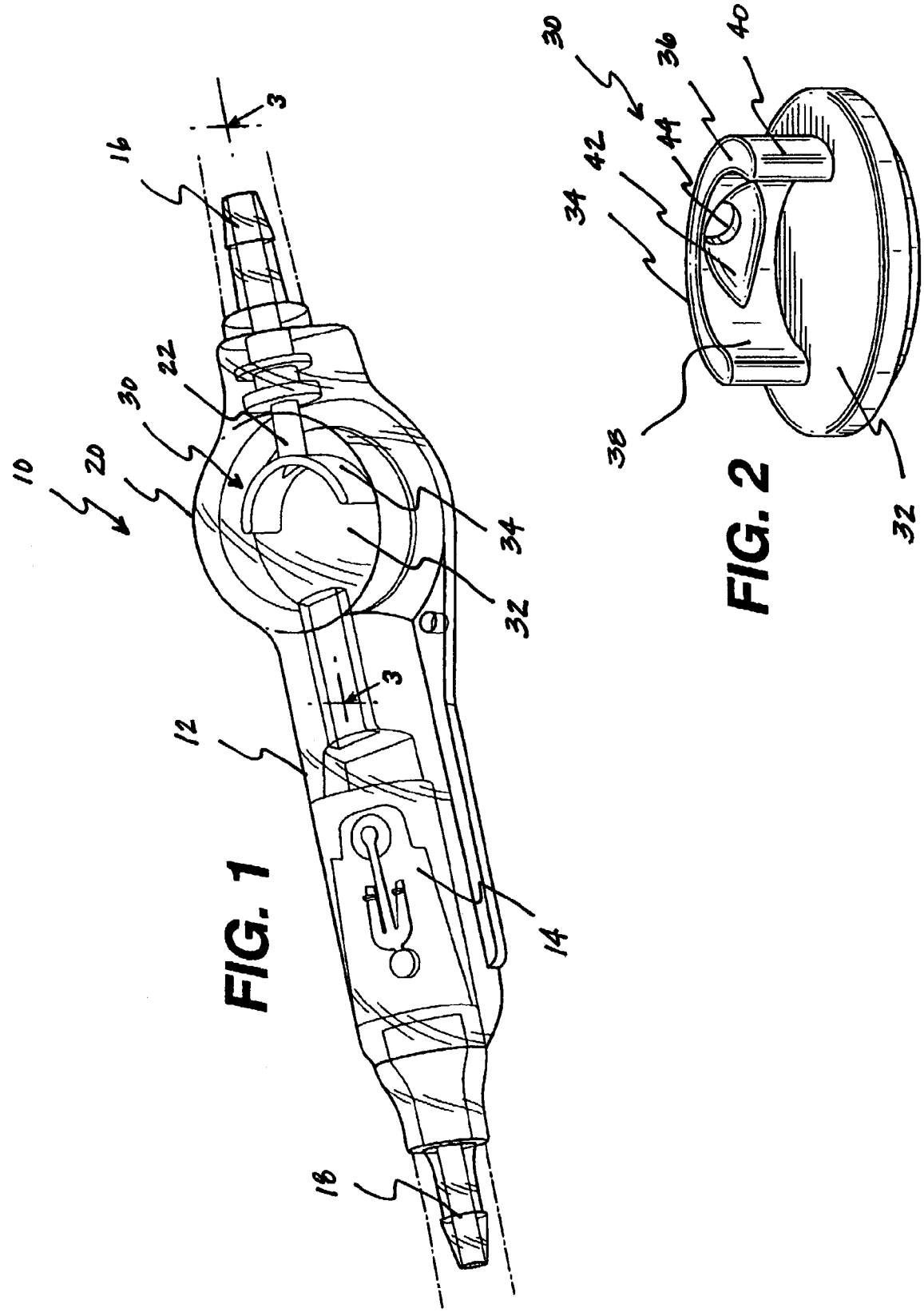

NEEDLE GUARD HAVING INHERENT PROBE DIRECTING FEATURES

CROSS-REFERENCE TO RELATED APPLICATIONS

Not applicable.

STATEMENT REGARDING FEDERALLY SPONSORED RESEARCH

Not Applicable.

FIELD OF THE INVENTION

The present invention relates to shunt systems for directing bodily fluids from one region of a patient to another region. More specifically, this invention relates to in-line shunt valves for regulating fluid flow into and out of the system and methods for shunt revision after occlusion or blockage of the ventricular catheter. Even more specifically, the invention relates to a needle guard with inherent probe directing features for use in ventricular catheter revisions of in-line configured shunt systems.

BACKGROUND OF THE INVENTION

Hydrocephalus is a condition afflicting patients who are unable to regulate cerebrospinal fluid flow through their body's own natural pathways. Produced by the ventricular system, cerebrospinal fluid (CSF) is normally absorbed by the body's venous system. In a patient suffering from hydrocephalus, the cerebrospinal fluid is not absorbed in this manner, but instead accumulates in the ventricles of the patient's brain. If left untreated, the increasing volume of fluid elevates the patient's intracranial pressure and can lead to serious medical conditions such as subdural hematoma, compression of the brain tissue, and impaired blood flow.

The treatment of hydrocephalus has conventionally involved draining the excess fluid away from the ventricles and rerouting the cerebrospinal fluid to another area of the patient's body, such as the abdomen or vascular system. A drainage system, commonly referred to as a shunt, is often used to carry out the transfer of fluid. In order to install the shunt, typically a scalp incision is made and a small hole is drilled in the skull. A proximal, or ventricular, catheter is installed in the ventricular cavity of the patient's brain, while a distal, or drainage, catheter is installed in that portion of the patient's body where the excess fluid is to be reintroduced. To regulate the flow of cerebrospinal fluid and maintain the proper pressure in the ventricles, a pump or one-way control valve can be placed between the proximal and distal catheters. Such valves can comprise a ball-in-cone mechanism as illustrated and described in U.S. Pat. Nos. 3,886,948, 4,332,255, 4,387,715, 4,551,128, 4,595,390, 4,615,691, 4,772,257, and 5,928,182, all of which are hereby incorporated by reference. The valves can be configured with inlet and outlet ends extending at a 90 degree angle to one another, thereby enabling the ventricular and drainage catheters that attach to these ends to form a right angle when implanted. Alternatively, the valves can include inlet and outlet ends extending at 180 degrees to one another so as to form an in-line configuration when assembled with the ventricular and drainage catheters. When properly functioning, these shunt systems provide an effective manner of regulating CSF in hydrocephalus patients.

After implantation and use over extended periods of time, these shunt systems tend to malfunction due to shunt occlusion. Frequently, the blockage occurs within the ventricular catheter. The obstruction can result from a number of problems, such as clotting, bloody CSF, excess protein content in the CSF, inflammatory or ependymal cells, brain debris, infection, or by choroid plexus or brain parenchyma in-growth through the openings of the ventricular catheter. Another potential cause of ventricular catheter occlusion is a condition known as slit ventricle syndrome in which the ventricular cavity collapses, thus blocking the openings of the ventricular catheter. If left untreated, the occlusion of the ventricular catheter can slow down and even prevent the ability of the shunt valve to refill, thereby rendering the shunt system ineffective.

In the past, the remedy for a clogged proximal catheter was to surgically remove and replace the catheter, which involved the risk of damage to the brain tissue or hemorrhage. The current trend is to rehabilitate the catheter in place through less invasive means. This can be accomplished in a procedure generally known as shunt or ventricular catheter revision which involves reaming the clogged catheter in its implanted state until the blockage is removed to thereby reestablish CSF flow through the ventricular catheter. Many shunt valves, such as the ones described in U.S. Pat. Nos. 4,816,016 and 5,176,627, are provided with a domed silicone reservoir that enables access to the attached ventricular catheter so that the system can be flushed out for this very reason. The self-sealing silicone dome can be pierced with a small needle to gain entry to the attached catheter, without affecting the ability of the dome to re-seal after the needle has been withdrawn. In domed valves with right angle access, i.e., where the ventricular catheter extends at a 90 degree angle to the drainage catheter, a surgeon can gain entry to the clogged ventricular catheter percutaneously by inserting a rigid endoscopic instrument such as an endoscopic cutting tool or endoscopic electrode through the dome of the valve and straight down to the attached catheter. Thereafter, the obstruction can be cleared by cutting, cauterizing, or coagulating using the endoscopic instrument.

Where the shunt valve forms an in-line configuration with the ventricular catheter, a greater amount of manipulation is required to access the attached catheter. Rather than being able to enter the catheter by inserting the endoscope instrument straight down through the domed reservoir, the surgeon must enter the domed reservoir at an angle and then manipulate the endoscopic instrument once inside the shunt valve until the opening of the catheter is reached. This poses a unique set of problems when performing shunt or catheter revisions on in-line configured shunt valves. If the surgeon overshoots or undershoots the angle of entry, he may risk puncturing the soft side walls of the valve, which are typically formed from a soft plastic, and damaging the system. There is thus a need for a device that will direct the endoscopic instrument once it is inside a domed reservoir of an in-line shunt valve towards the attached ventricular catheter, while preventing inadvertent puncturing of the shunt valve by the instrument.

SUMMARY OF THE INVENTION

The present invention provides a needle or puncture guard that has inherent probe directing features for use in an in-line configured shunt valve. The guard comprises a base member configured for mounting within the domed reservoir of the shunt valve, and a guide wall seated on the base member.

The guide wall is defined by a top wall, an inner side wall, and an opposed outer side wall. The inner side wall has an indented section with an aperture extending through the indented section. The inner side wall can be concavely curved, and the guide wall itself can be C-shaped. The indented section forms a dimple or notch on the inner side wall, and can have an oval or almond shape, while the aperture can be a round hole. The indented section can also have a radius of curvature in the range of about 30° to about 45°. To help surgeons detect the shunt valve by x-ray, the guard can include a radiopaque marker. The radiopaque marker can be shaped like an arrow to indicate the flow direction of the shunt valve. Furthermore, the radiopaque marker can also be embedded within the base member.

Also provided is a fully assembled shunt device for draining fluid within a patient, in which the shunt device comprises a housing having a valve mechanism therein for regulating fluid flow into and out of the shunt device. The shunt device also includes an inlet port configured to receive a ventricular catheter, an outlet port configured to receive a drainage catheter, and a domed reservoir in fluid communication with the inlet port. The domed reservoir can be formed from a self-sealing silicone. Within the domed reservoir is mounted the needle or puncture guard of the present invention. The guard has a base member and a guide wall seated on the base member. The guide wall is defined by a top wall, an inner side wall, and an opposed outer side wall. The inner side wall has an indented section with an aperture extending through the indented section. The aperture extends into a channel in fluid communication with the inlet port. The shunt device can be configured as an in-line valve, with the inlet port and outlet port extending at a 180° angle with respect to each other.

The present invention also provides a method for performing a percutaneous catheter revision on a shunt system having a blocked ventricular catheter. The catheter revision involves providing a shunt system having a shunt device with a needle or puncture guard as previously described. Connected to the inlet port is a ventricular catheter, while a drainage catheter is connected to the outlet port. When the ventricular catheter is obstructed, the surgeon exposes the domed reservoir of the shunt device, then punctures the domed reservoir with a catheter needle. The surgeon then inserts the catheter needle into the reservoir until it contacts the guide wall of the puncture guard. The curvature of the inner side wall of the guide wall will funnel the needle towards the indented section, whose curvature then directs the needle towards the aperture. The surgeon next threads a flexible endoscopic instrument through the catheter needle, maneuvering the instrument until the tip contacts the aperture. As more force is exerted onto the instrument, the flexible instrument will bend and extend through the aperture and into the ventricular catheter. Once the tip is able to pass through to the ventricular catheter, the surgeon can use the instrument to remove the obstruction by cutting, cauterizing, coagulating, blasting, or vaporizing the obstruction. Alternatively, the instrument can be used to place an intracranial sensor within the ventricular catheter.

Further features of the invention, its nature and various advantages, will be more apparent from the accompanying drawings and the following detailed description of the drawings and the preferred embodiments.

BRIEF DESCRIPTION OF THE DRAWINGS

The invention can be more fully understood from the following detailed description taken in conjunction with the accompanying exemplary drawings, though not necessarily drawn to scale, in which:

FIG. 1 is a perspective view of a fully assembled shunt valve with a needle guard of the present invention;

FIG. 2 is a perspective view of the needle guard of FIG. 1;

DETAILED DESCRIPTION OF THE INVENTION

Figure 7:
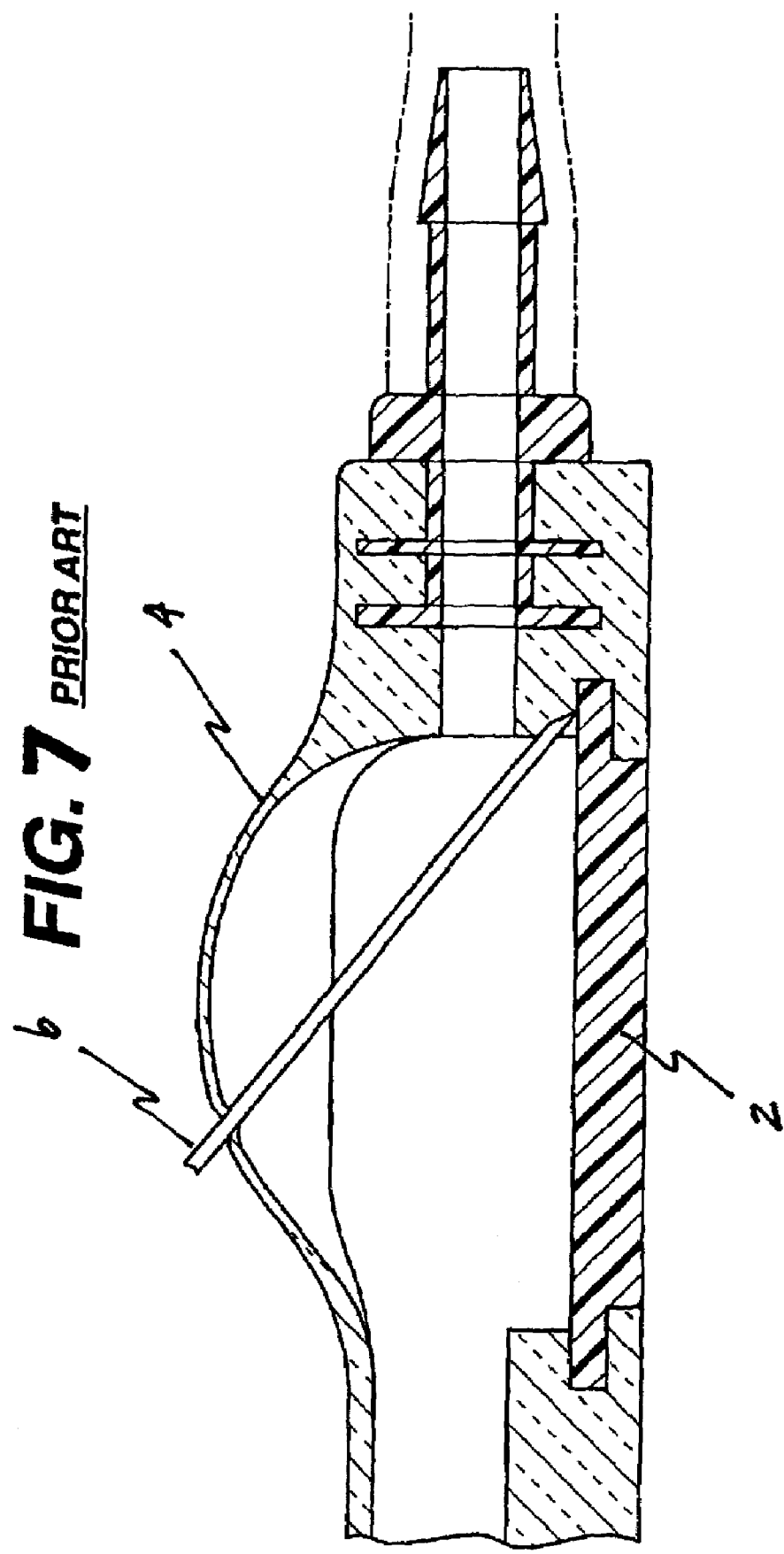
FIG. 7 is a cross-sectional view of a shunt valve of the prior art.

The present invention provides a needle or puncture guard that has inherent probe directing features for use in an in-line configured shunt valve. In addition to protecting the soft side walls of the shunt valve 4 against punctures from needle 6 as does the guard 2 of the prior art, an example of which is depicted in FIG. 7, the guard of the present invention also inherently guides the needle into proper alignment during catheter revisions of in-line shunt valves. Turning now to the drawings and particularly to FIG. 1, a shunt device 10 having a needle or puncture guard 30 in accordance with the present invention is shown. The shunt device 10 includes a housing 12 within which there resides a valve mechanism 14 for regulating fluid flow into and out of the shunt device 10. The valve mechanism 14 can comprise any typical valve mechanism, such as the ball-in-cone valve illustrated and as described in U.S. Pat. Nos. 3,886,948, 4,332,255, 4,387,715, 4,551,128, 4,595,390, 4,615,691, 4,772,257, and 5,928,182, all of which are hereby incorporated by reference. Of course, it is understood that the valve mechanism 14 can also comprise other suitable valves including programmable valves for controlling fluid flow in a shunt device as are known in the art.

An inlet port 16 is provided for attachment to a ventricular catheter that is to be implanted in a ventricular cavity of a hydrocephalus patient. The outlet port 18 is configured to attach to a drainage catheter which would be placed in the region of the patient such as the peritoneal cavity where excess cerebrospinal fluid is to be reintroduced. Also included with the shunt device 10 is a domed reservoir 20 that is in fluid communication with the inlet port 16 by way of channel 22. The domed reservoir 20 can be formed from a self-sealing silicone as is well known in the art, thereby enabling a needle to puncture the silicone dome for access to the shunt device 10 while still providing a seal to form upon withdrawal of the needle from the reservoir 20. The shunt device 10 has an in-line configuration, i.e., the inlet and outlet ports 16, 18 extend at an angle of about 180° with respect to one another.

Mounted within the domed reservoir 20 is a needle or puncture guard 30 having inherent probe directing features as shown in further detail in FIG. 2. The guard 30 comprises a base member 32 on which there is seated a guide wall 34.

Figure 3:
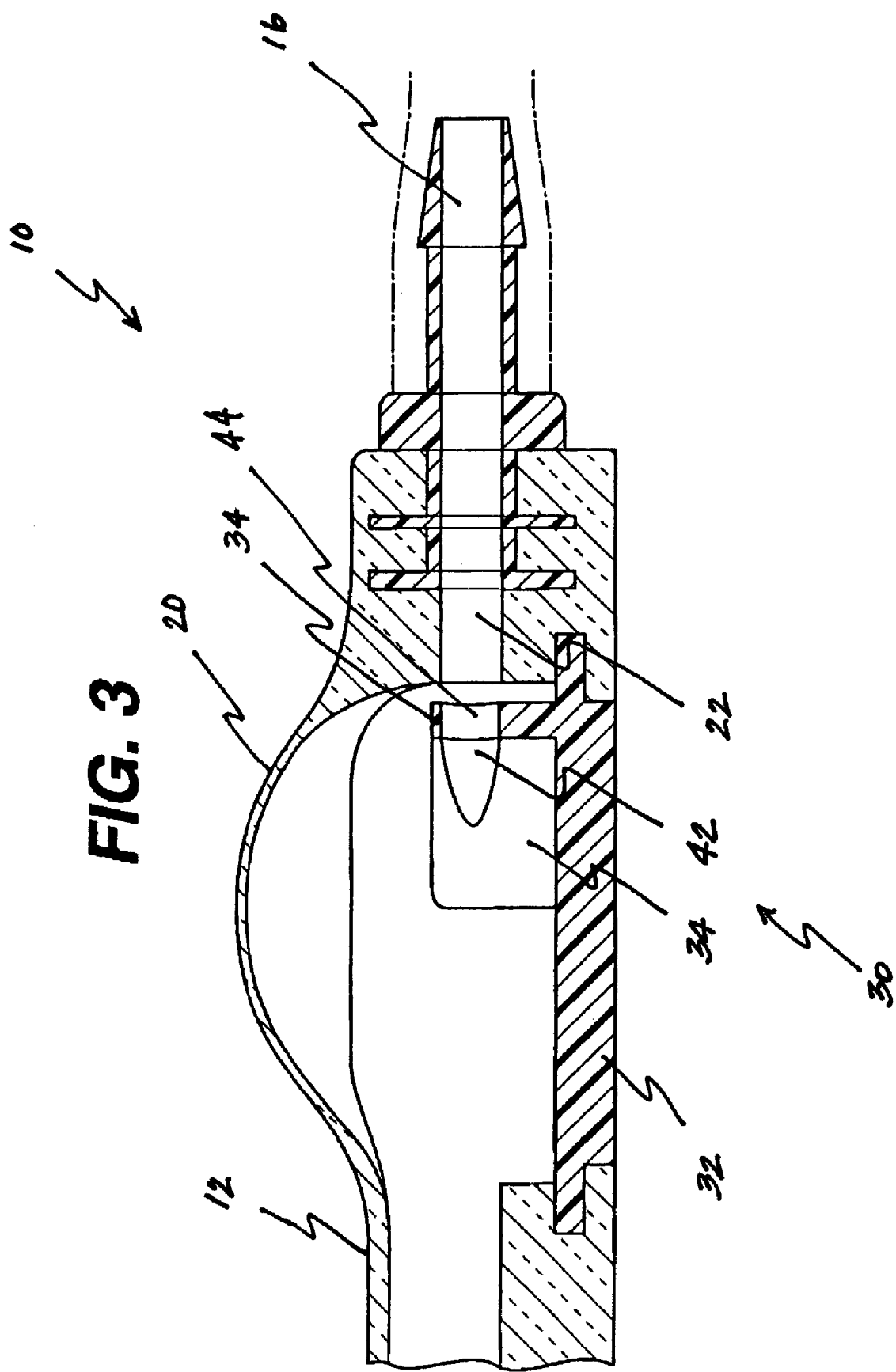
FIG. 3 is a cross-sectional view of a portion of the shunt valve and needle guard of FIG. 1 along lines 3—3.

As illustrated in FIG. 3, the base member 32 can be incorporated into the housing 12 of the shunt device 10. The guide wall 34 is defined by a top wall 36, an inner side wall 38 and an opposed outer side wall 40. The inner side wall 38 includes an indented section 42 that contains an aperture 44 extending through the indented section 42. As shown, the guide wall 34 can be curved. For instance, the inner side wall 38 can be concavely curved, and furthermore the entire guide wall 34 can be C-shaped or assume an arc-like shape. The indented section 42 forms a dimple or notch on the inner side wall 38 of the guide wall 34, and can be shaped like an oval or almond.

To provide the guide wall 34 with its inherent probe directing features, the indented section 42 can be formed with a curvature so as to guide any instrument, tool or probe that is urged against the indented section 42 towards the aperture 44. It is contemplated that the radius of curvature of the indented section 42 is in the range of about 30° to about 45°. This smooth, curved surface enables the indented section 42 to create a funneling action when a probe or needle is pushed against it, thereby directing the probe or needle to the exit hole or aperture 42. As illustrated in FIG. 2, the aperture 44 can be a round hole. However, it is understood that the aperture 44 can have any shape and size suitable for allowing an endoscopic instrument to be inserted through.

Figure 4:
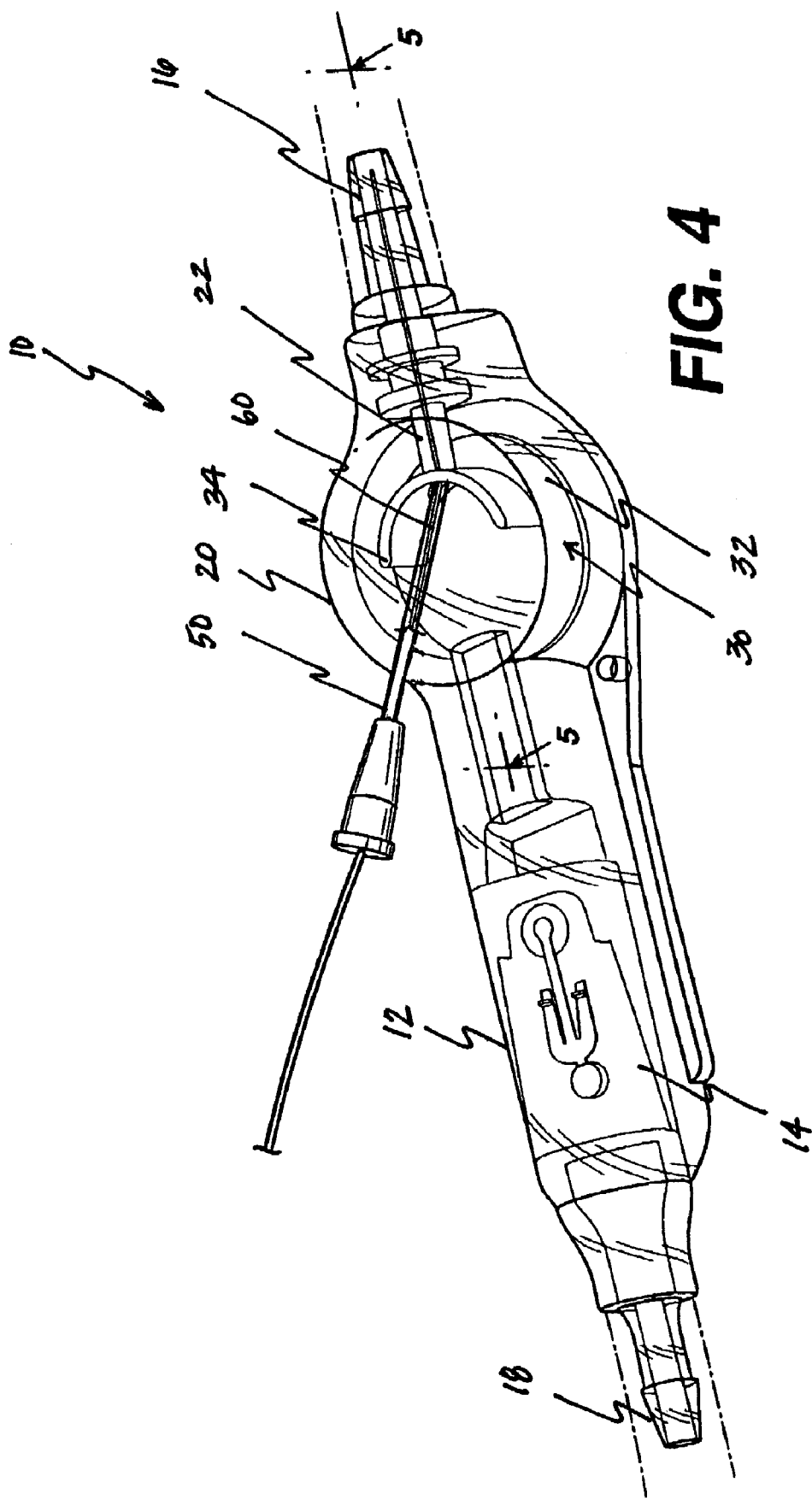
FIG. 4 illustrates an endoscopic instrument being placed into the shunt valve and needle guard of FIG. 1.
Figure 5:
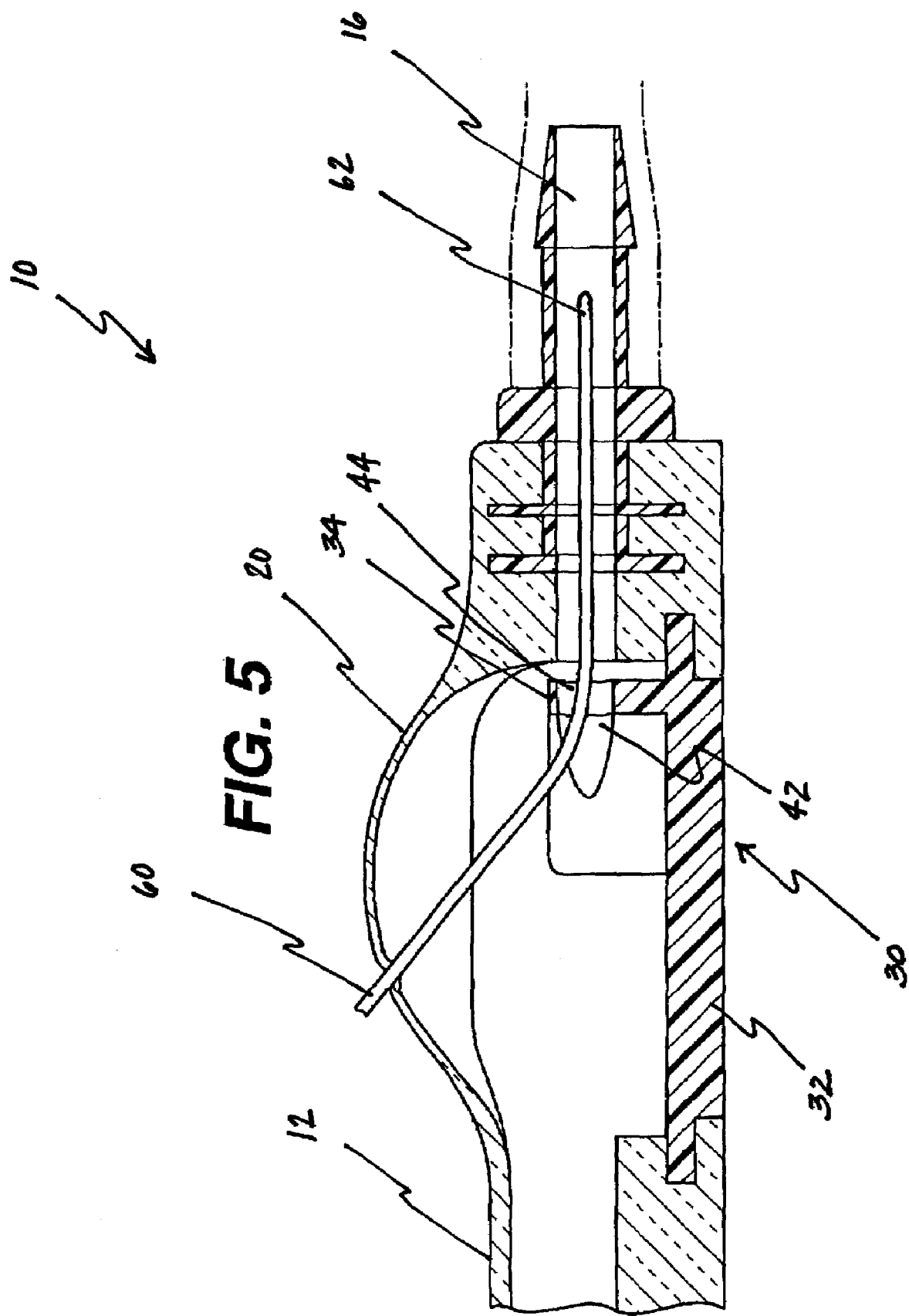
FIG. 5 is a cross-sectional view of a portion of the endoscopic instrument inside the shunt valve and needle guard of FIG. 4 along lines 5—5.

The needle or puncture guard 30 of the present invention can be useful for guiding a flexible endoscopic instrument through the domed reservoir of the shunt device 10 and into an attached ventricular catheter during catheter revisions of in-line shunt valves. FIGS. 4 and 5 show an exemplary in-line shunt device 10 having mounted within the domed reservoir 20 a needle guard 30. To perform a catheter revision on a blocked ventricular catheter attached to shunt device 10, the surgeon would first surgically expose the domed reservoir 20 of the shunt device 10, then puncture the domed reservoir 20 with a catheter needle 50. The catheter needle 50 is urged towards the inlet port 16 until it pushes up against the needle guard 30. The curvature of the inner side wall 38 of the guide wall 34 directs the needle 50 towards the indented section 42. When the needle 50 reaches the indented section 42, its smooth curved surface will funnel the needle 50 towards the exit hole or aperture 44. At this point, the surgeon then threads a flexible endoscopic instrument, tool or probe 60 through the catheter needle 50, maneuvering the instrument 60 until the tip 62 bends and extends into the aperture 44. As more force is exerted against the instrument 60, the tip 62 of the flexible endoscopic instrument will then extend through the aperture 44, into the attached channel 22, and into the ventricular catheter as illustrated in FIG. 5.

Once the tip 62 is able to pass through to the catheter, the surgeon can use the instrument 60 to remove the obstruction from the ventricular catheter. Suitable instruments 60 for performing the removal include endoscopic electrodes, ultrasonic, and/or cutting tools which enables the surgeon to cut up, cauterize, coagulate, blast, or vaporize the obstruction. After the obstruction is removed, CSF can then re-enter the ventricular catheter and the shunt valve can then properly refill. It is contemplated that the same basic procedure can be used to insert a monitoring device into the ventricular catheter. For example, rather than using a removal tool, the endoscopic instrument 60 can be a sensor delivery tool for delivering an intracranial pressure (ICP) sensor within the ventricular catheter.

The needle guard 30 of the present invention can be formed from a hard plastic to prevent tools such as the catheter needle 50 and endoscopic instrument 60 from inadvertently puncturing the soft side walls of the domed reservoir 20. For example, lubricious plastics such as nylon, polytetrafluoroethylene (PTFE), or acetal polymers are suitable materials for making the needle guard 30. However, it is understood that the materials are not limited to those listed here and can include other biocompatible materials having the appropriate physical properties to prevent against needle punctures.

Figure 6:
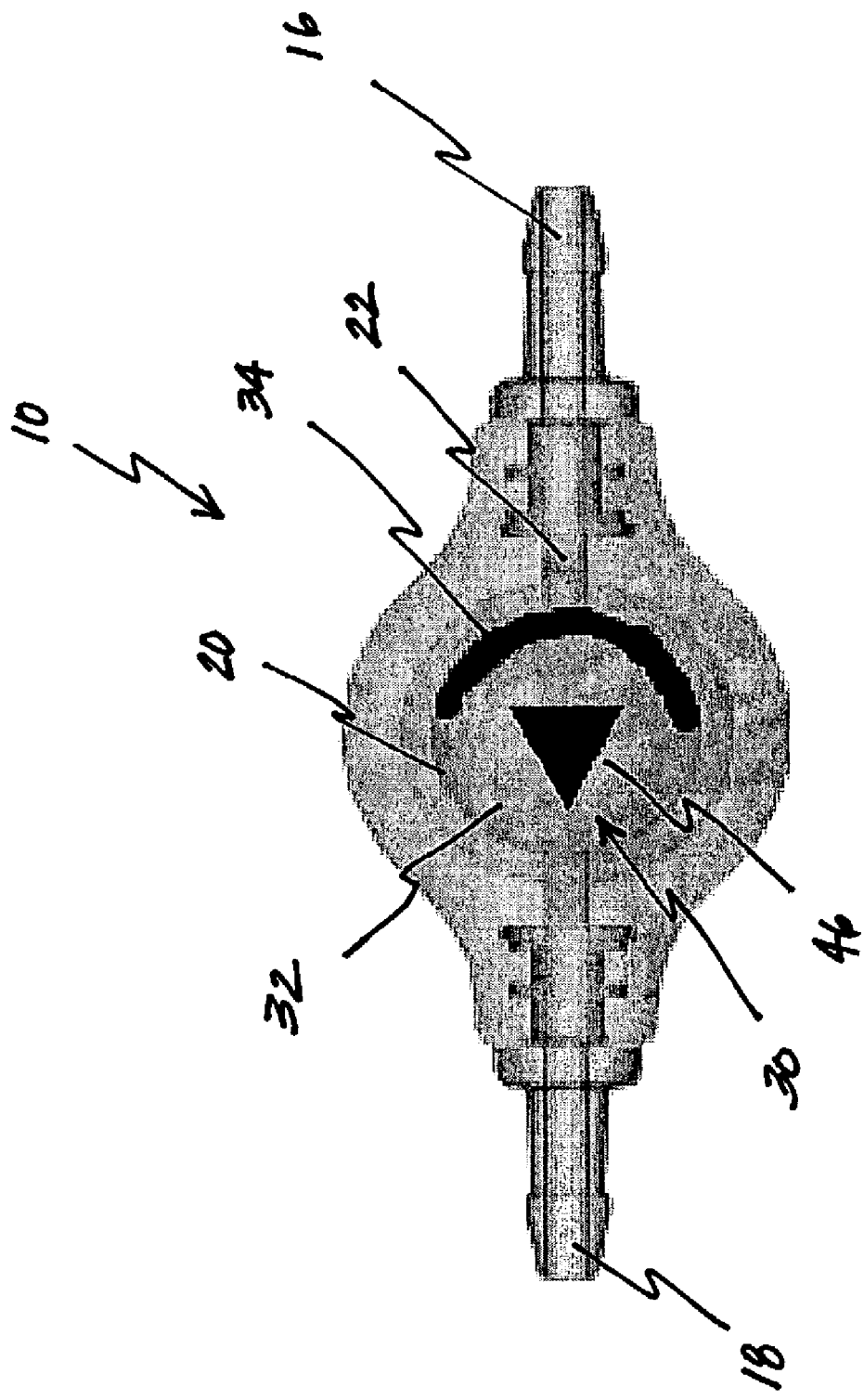
FIG. 6 is a top-down view of another embodiment of the needle guard of the present invention.

To provide even greater benefit to the surgeon, the needle guard 30 of the present invention can include a radiopaque marker 46. As shown in FIG. 6, the radiopaque marker 46 can be shaped like an arrow to indicate the flow direction of the shunt device 10. The radiopaque marker 46 can be made from any x-ray detectable material. For example, the marker 46 can be formed from tantalum powder in a silicone adhesive base for attachment to the needle guard 30. Alternatively, the radiopaque marker 46 can also be embedded within the base member 32. This radiopaque marker 46 will be recognizable on x-ray and will also help the surgeon in surgical placement to correctly align the shunt device 10 for flow direction. It is contemplated that the guide wall 34 can also be provided with a similar radiopaque marker for identifying shunt devices 10 containing the needle guard 30 of the present invention after the shunt devices have been implanted.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A puncture guard for use in a shunt valve having a domed silicone reservoir, comprising:
   a base member configured for mounting within the domed silicone reservoir of the shunt valve; and
   a guide wall seated on the base member, the guide wall being defined by a top wall, an inner side wall, and an opposed outer side wall, the inner side wall having thereon an indented section and an aperture extending through the indented section.

2. The guard of claim 1, wherein the inner side wall is concavely curved.

3. The guard of claim 2, wherein the guide wall is C-shaped.

4. The guard of claim 1, wherein the indented section is shaped like an oval.

5. The guard of claim 1, wherein the indented section has a radius of curvature in the range of about 30° to about 45°.

6. The guard of claim 1, wherein the aperture is a round hole.

7. The guard of claim 1, further including a radiopaque marker.

8. The guard of claim 7, wherein the radiopaque marker is shaped like an arrow.

9. The guard of claim 7, wherein the radiopaque marker is embedded within the base member.

10. A shunt device for draining fluid within a patient, comprising:
    a housing having a valve mechanism therein for regulating fluid flow into and out of the shunt device, an inlet port configured to receive a ventricular catheter, an outlet port configured to receive a drainage catheter, and a domed reservoir in fluid communication with the inlet port, the domed reservoir further including a puncture guard having a base member and a guide wall seated on the base member, the guide wall being defined by a top wall, an inner side wall, and an opposed outer side wall, the inner side wall having thereon an indented section and an aperture extending through the indented section.

11. The device of claim 10, wherein the aperture extends into a channel in fluid communication with the inlet port.

12. The device of claim 10, wherein the inlet port and outlet port extend at a 180° angle with respect to each other.

13. The device of claim 10, wherein the domed reservoir is formed from a self-sealing silicone.

14. The device of claim 10, wherein the inner side wall is concavely curved.

15. The device of claim 14, wherein the guide wall is C-shaped.

16. The device of claim 10, wherein the indented section is shaped like an oval.

17. The device of claim 10, wherein the indented section has a radius of curvature in the range of about 30° to about 45°.

18. The device of claim 10, wherein the aperture is a round hole.

19. The device of claim 10, further including a radiopaque marker.

20. The device of claim 19, wherein the radiopaque marker is shaped like an arrow.

21. The device of claim 19, wherein the radiopaque marker is embedded within the base member.

22. A method of performing a percutaneous catheter revision on a shunt system having a blocked ventricular catheter, comprising the steps of:

providing a shunt system having a shunt device with a valve mechanism therein for regulating fluid flow into and out of the shunt device, an inlet port connected to a ventricular catheter, an outlet port connected to a drainage catheter, and a domed reservoir in fluid communication with the inlet port, the domed reservoir further including a puncture guard having a base member and a guide wall seated on the base member, the guide wall being defined by a top wall, an inner side wall, and an opposed outer side wall, the inner side wall having thereon an indented section and an aperture extending through the indented section;

surgically exposing the domed reservoir;

puncturing the domed reservoir with a catheter needle;

threading a flexible endoscopic instrument through the catheter needle;

inserting a tip of the flexible endoscopic instrument through the aperture; and extending the tip of the flexible endoscopic instrument into the ventricular catheter.

23. The method of claim 22, further including the step of removing an obstruction from the ventricular catheter.

24. The method of claim 23, wherein the step of removing the obstruction includes cutting, cauterizing, coagulating, blasting, or vaporizing.

25. The method of claim 22, further including the step of placing an intracranial sensor within the ventricular catheter.

* * * * *